US006403123B1

(12) United States Patent
Scott et al.

(10) Patent No.: US 6,403,123 B1
(45) Date of Patent: Jun. 11, 2002

(54) METHOD FOR TOPICAL TREATMENT OF ANTHRALIN-RESPONSIVE DERMATOLOGICAL DISORDERS

(76) Inventors: Eugene J. Van Scott, 3 Hidden La., Abington, PA (US) 19001; Ruey J. Yu, 4 Lindenwold Ave., Ambler, PA (US) 19002

( * ) Notice: Subject to any disclaimer, the term of this patent is extended or adjusted under 35 U.S.C. 154(b) by 0 days.

(21) Appl. No.: 09/664,828

(22) Filed: Sep. 19, 2000

(51) Int. Cl.[7] .............................. A61K 9/14; A61K 9/00; A61K 9/70
(52) U.S. Cl. ..................... 424/489; 424/400; 424/401; 514/861; 514/863
(58) Field of Search ................................ 424/400, 443, 424/484, 489, 78.02, 78.03, 401; 514/861, 863

(56) References Cited

U.S. PATENT DOCUMENTS

| | | | |
|---|---|---|---|
| 3,904,766 A | | 9/1975 | Van Scott et al. |
| 4,067,975 A | | 1/1978 | Yu et al. |
| 4,141,977 A | | 2/1979 | Yu et al. |
| 4,203,969 A | * | 5/1980 | Yarrow et al. ................. 424/83 |
| 4,216,224 A | | 8/1980 | Yu et al. |
| 4,258,052 A | | 3/1981 | Yu et al. |
| 4,287,214 A | | 9/1981 | Van Scott et al. |
| 4,361,571 A | | 11/1982 | Van Scott et al. |
| 4,367,224 A | | 1/1983 | Van Scott et al. |
| 4,892,888 A | * | 1/1990 | Grollier et al. .............. 514/132 |
| 5,476,664 A | * | 12/1995 | Robinson et al. ............ 424/443 |
| 6,146,636 A | * | 11/2000 | Breton et al. ............. 424/195.1 |

* cited by examiner

*Primary Examiner*—Thurman K. Page
*Assistant Examiner*—Charesse L. Evans
(74) *Attorney, Agent, or Firm*—Akin, Gump, Strauss, Hauer & Feld, L.L.P.

(57) ABSTRACT

The staining of skin and clothing incidental to the topical application of anthralin may be avoided or eliminated by: (a) topically applying an anthralin formulation containing a therapeutically effective amount of anthralin to the involved area of the skin; and (b) topically applying a wax formulation to the involved area, wherein the wax formulation comprises a wax. In addition, a powder may be topically applied to the involved area.

19 Claims, No Drawings

METHOD FOR TOPICAL TREATMENT OF ANTHRALIN-RESPONSIVE DERMATOLOGICAL DISORDERS

BACKGROUND OF THE INVENTION

The present invention relates to the treatment of dermatological disorders, including psoriasis and eczema. Specifically, the present invention relates to a method of treating anthralin-responsive dermatological disorders by a method of topical application of anthralin that results in minimal or no staining of skin or clothing.

In human skin, certain inflammatory disorders, such as psoriasis, eczema and other dermatoses, may involve a disturbed keratinization with scale formation. The causes of most inflammatory dermatoses are unknown, although immunologic and genetic factors appear to be involved in the development of these diseases. Psoriasis is a chronic inflammatory skin disease characterized by persistent erythema and silvery scales, and remains a disfiguring and disabling cutaneous impairment to millions of people. In the United States, the disease affects approximately 2% of the population. Eczema is also a chronic skin disease and is characterized by persistent itch with erythema and some scales. Since the etiologies of these diseases are unknown, preventions remain inconceivable, and known therapies are empiric.

In psoriasis, photochemotherapy with psoralens plus UVA and systemic treatments with well-known drugs or experimental agents provide short-term remission of the disease. Such drugs include methotrexate, cyclosporin, retinoids, fumaric acid esters, glucocorticoids, liarozole, tacrolimus, anti-CD4-antibodies, interleukin, diphtheria fusion toxin and ascomycin derivatives. Treatment using these drugs can result in immunosuppression, leading to serious infections, cancers, acute and chronic toxicity on liver, kidney and bones, etc. Thus, clinicians have shifted their focus to external or topical treatment of psoriasis, eczema and similar dermatological disorders.

Topical treatments with tar, tazarotene, glucocorticoids or vitamin $D_3$ analogues, such as calcipotriene, have provided various degrees of temporary remission. However, use of these compounds can be associated with degrees of tachyphylaxis, non-responsiveness and/or rebound worsening.

Anthralin, also known as dithranol, was introduced for topical use in 1916 and continues to be in use for topical treatment of psoriasis and eczema because of its efficacy and safety profile. Anthralin is chemically identified as 1,8,9,-anthracenetriol or 1,8-dihydroxyanthrone, and has a molecular weight of 226 ($C_{14}H_{10}O_3$). Anthralin is known to be effective topically in the treatment of psoriasis, chronic eczemas, dermatophytoses, alopecia areata, and other skin disorders. In topical treatment of psoriasis with anthralin, substantial clearing of chronic plaques usually occurs within two months, and the duration of improvement is decidedly longer than that following topical corticosteroids.

Two undesirable side effects are presently associated with the topical use of anthralin: (1) skin irritation; and (2) staining of the skin, clothing and other items which come in contact with treated areas of the skin. The skin irritation from anthralin is dose-related; therefore, in order to minimize irritation, low concentrations of anthralin are preferable. The second side effect, staining, has, up to the present time, been less manageable. When commercially available products are used for topical treatment of psoriasis or eczema, anthralin can stain the skin and hair various colors ranging from brownish, greenish, to purple colors depending on factors such as pH and the composition of the vehicle by which the anthralin is administered. Removal of the stains from pillowcases, bed sheets and clothing is very difficult, and usually impossible. These adverse effects have discouraged topical use of anthralin products for the treatment of psoriasis, eczema and other dermatoses.

Previously, we have discovered that dithranol (anthralin) for use in the treatment of dermatological disorders may be protected from oxidation when it is present in a composition containing either an antitoxidant alpha hydroxyacid or oxalic acid. Such compositions and methods are disclosed in detail in U.S. Pat. Nos. 4,287,214 and 4,367,224. Although the compositions and related methods of these patents describe compositions for topical application of anthralin to the skin, the problem of staining of the skin, linens or clothing by the anthralin is not addressed.

BRIEF SUMMARY OF THE INVENTION

We have discovered that the staining of the skin and clothing incidental to the topical use of anthralin can be averted or minimized by a simple method of application.

By use of the method of the present invention, anthralin-responsive dermatological disorders can be treated using anthralin with minimal or no staining to the skin, linens and clothing. Specifically, the invention provides a method of treating dermatological disorders in a human comprising: (a) topically applying an anthralin formulation containing a therapeutically effective amount of anthralin to the involved area of the skin of the human, and (b) topically applying a wax formulation to the involved area, wherein the wax formulation comprises a wax. The topical application of the anthralin formulation may be in the form of a liquid, a gel, a lotion or a cream.

The anthralin is present in the anthralin formulation in a concentration of about 0.05% to about 10% by weight. In the most preferred aspects of the invention, anthralin is resent in the anthralin formulation in a concentration of about 0.1% to about 5% by weight, ore preferably about 0.1% to about 1% by weight.

Wax provided for use in the wax formulation of the method of the present invention may be preferably selected from the group consisting of beeswax, ceresin, paraffin and mixtures thereof. The wax formulation, in addition to comprising a wax, may also comprise a wax vehicle.

According to the present invention, wax is present in the wax formulation in a concentration of about 1% to about 80% by weight, preferably about 5% to about 60% by weight, or, more preferably, about 10% to about 40% by weight.

The method of the present invention preferably further comprises the step of topically applying a powder to the involved skin area. This powder may be selected from the group consisting of talc, starch powder, cellulose powder, and oatmeal powder and mixtures thereof.

As used herein, a "therapeutically effective amount" of anthralin is that amount of anthralin that is sufficient to provide a beneficial effect on the dermatological disorder(s) of the patient to whom it is administered.

As used herein, "dermatological disorder(s)" means skin diseases including psoriasis, eczema and other anthralin-responsive skin disorders.

As used herein, "treating" means applying or administering a medication to an area affected by a dermatological disorder in order to improve and/or irradiate the dermatological disorder(s) and/or the symptoms of the dermatological disorder.

As used herein, the term "wax formulation" is meant to encompass compositions having substantially 100% wax by weight, mixtures of wax combined with a solvent or solvents or other dermatologically acceptable vehicles, and/or wax combined with other additives such as cholesterol, mineral oil, lemon oil, vanillin, coconut oil, emulsifiers such as polysorbate 80 and sorbitan sesquioleate.

DETAILED DESCRIPTION OF THE INVENTION

Anthralin for use in the anthralin formulation of the present invention may be provided in any form known in the art, including solution, gel, lotion and powder form. Anthralin may be present in the anthralin formulation in any therapeutically effective amount; however the preferred concentration is in the range of about 0.01% to about 50% by weight or about 0.05% to about 10% by weight. Alternatively, preferred concentrations are in the range of about 0.1% to about 5% by weight, more preferably about 0.1% to about 1% by weight.

The anthralin formulation for use in the method of the present invention may take the form of a liquid, a gel, a cream, a lotion or the like. The anthralin may be dissolved in a solvent in order to form a liquid anthralin formulation. The anthralin solvent may be any suitable non-toxic, dermatologically acceptable substance known in the art in which anthralin may be dissolved. Examples of anthralin solvents for use in the present invention include, but are not limited to, ethanol, propylene glycol, butylene glycol, diisopropyl adipate, diethyl tartrate, triethyl citrate, isopropyl myristate, isopropyl palmitate, ethoxy diglycol, isododecane, isohexadecane, or isoeicosane or mixtures thereof.

Antioxidant(s) may be added to the anthralin formulation to prevent oxidation of the anthralin upon contact with air. Such antioxidants include, but are not limited to, oxalic acid, N-acetyl cysteine, citric acid, isocitric acid, ascorbic acid, isoascorbic acid, tartaric acid, malic acid, gluconolactone and mixtures thereof. Other antioxidant(s) and methods for use in anthralin formulations are detailed in our U.S. Pat. No. 4,367,224, entitled "Stable Dithranol Compositions in Anhydrous Vehicles", and U.S. Pat. No. 4,287,214, entitled "Dithranol Compositions Stabilized with Alpha Hydroxy Acids", the disclosures of which are incorporated herein by reference. The total concentration of antioxidant(s) for use in the anthralin formulation of the present invention may range from about 0.01% to about 5% by weight, with a preferred range of about 0.01% to about 2% by weight.

The wax for use in the wax formulation of the present invention may be selected from any suitable non-toxic, dermatologically acceptable waxes known in the art. For example, waxes useful in the wax formulation of the present invention include, but are not limited to, apple peel wax, avocado wax, bayberry wax, beeswax, candelilla wax, carnauba wax, ceresin, cetyl esters, jojoba wax, lanolin wax, mink wax, montan wax, orange peel wax, ouricury wax, ozokerite, palm kernel wax, paraffin, PEG-beeswax, PEG-camauba wax, rice wax, shellac wax, spent grain wax, synthetic beeswax, synthetic Japan wax, and other natural or synthetic waxes and mixtures thereof. The preferred waxes for use in the wax formulation of the present invention are beeswax, ceresin and paraffin.

When practicing the present invention, it is preferred that the total concentration of the selected wax or waxes present in the wax formulation be in the range of about 0.01% to about 99.9% by weight, with a preferred range of about 1% to about 80% by weight, and with a more preferred range of about 5% to about 60% by weight. The most preferred range of wax concentration is from about 10% to about 40% by weight.

In one particular aspect of the present invention, the wax formulation may be prepared by heating the selected wax (es) until it has completely melted and subsequently mixing it with a with a suitable non-toxic, dermatologically acceptable vehicle. The vehicle may be a solvent, such as any organic solvent known in the art, including those listed above as anthralin solvents for use in the anthralin formulation of this invention. Examples of solvents which may be used as vehicles for the wax include, but are not limited to, ethanol, isododecane and triethyl citrate.

In addition, emulsifiers and other additives may be included in the wax formulation. Such additives include, but are not limited to, cholesterol, mineral oil, lemon oil, vanillin, coconut oil, emulsifiers, such as polysorbate 80 and sorbitan sesquioleate, and mixtures thereof.

The powder for use in the method of the present invention can be any powder known in the art suitable for dermatological application. Such powders for use in the present invention include, but are not limited to aluminum silicate, aluminum starch octenylsuccinate, amylodextrin, attapulgite, bentonite, calamine, calcium silicate, cellulose, chalk, colloidal oatmeal, corn flour, corn starch, cyclodextrin, dextrin, diatomaceous earth, dimethylimidazolidinone corn starch, dimethyliminodazolidinone rice starch, fuller's earth, glyceryl starch, hectorite, hydrated silica, kaolin, loess, magnesium aluminum silicate, magnesium carbonate, magnesium hydroxide, magnesium oxide, magnesium silicate, magnesium trisilicate, maltodextrin, microcrystalline cellulose, montmorillonite, Moroccan lava clay, oat bran, oat flour, oatmeal, oat starch, phaseolus angularis bean starch, potassium aluminum polyacrylate, potato starch, pyrophyllite, rice starch, silica, sodium magnesium fluorosilicate, sodium polyacrylate starch, sodium starch octenylsuccinate, talc, wheat powder, wheat starch, wood powder, zeolite, other natural or synthetic absorbents and adsorbents and mixtures thereof. The preferred powders for use in the present invention are talc, starch powder, cellulose powder, and oatmeal powder. The more preferred powders are fine powders of talc and starch.

Finally, to formulate a synergistic or amplified composition, dermatologic gent(s) and/or topical agent(s) of cosmetic and/or pharmaceutical substances may be incorporated into the method of the present invention to amplify the bioactivity for the topical treatment of psoriasis, eczema, and other dermatological disorders. Such agents may be directly incorporated into the anthralin formulation. Alternatively, these agents may be applied to skin lesions separately, but substantially contemporaneously with the method.

Topical and dermatologic agents which may be incorporated into the method include, but are not limited to, antipsoriatic agents, antieczema and antidermatitis agents, antiwart agents, antihyperkeratotic and antikeratoses agents, antidandruff and antiseborrheic agents, antihistamine and antipruritic agents, antiinflammatory agents, antimicrobial agents, corticosteroids, retinoids, N-acetyl amino acids, vitamins, and coal tar. Examples of such include pramoxine, clotrimazole, ketoconazole, miconazole, econazole, fluconazole, metronidazole, hydroxyzine, terbinafine, diphenhydramine, lidocaine, procaine, mepivacaine, monobenzone, erythromycin, tetracycline, clindamycin, meclocycline, hydroquinone, minocycline, naproxen, ibuprofen, theophylline, cromolyn, betamethasone valerate, triamcinolone acetonide, fluocinonide, benzoyl peroxide, hydrogen peroxide, crotamiton, propranolol, promethazine, vitamin A palmitate, vitamin A acetate, and vitamin E acetate. Other examples include hydrocortisone, hydrocortisone 21-acetate, hydrocortisone 17-valerate, hydrocortisone 17-butyrate, triamcinolone acetonide, betamethasone dipropionate, clobetasol propionate, salicylic acid, retinoic acid, alpha hydroxyacids and O-acetyl derivatives such as mandelic acid, citric acid, gluconolactone, tartaric acid, malic acid, O-acetyl-mandelic acid, Nacetyl proline, menthol, camphor, phenol, urea, selenium sulfide, zinc pyrithione, and sulfur.

The anthralin used in the present invention may be in powder form, or any other form known in the art. In one embodiment of the invention, the anthralin formulation is formulated by dissolving anthralin powder in a solvent prepared from ethanol, propylene glycol, butylene glycol, diisopropyl adipate, diethyl tartrate, triethyl citrate, isopropyl myristate, isopropyl palmitate, ethoxy diglycol, isododecane, isohexadecane and/or isoeicosane. The concentration of anthralin may range from about 0.01% to about 50% by weight, with preferred range of about 0.05% to about 10% by weight, with more preferred range of about 0.1% to about 5% by weight and with most preferred range from about 0.1% to about 1% by weight. Antioxidant(s) such as oxalic acid, N-acetyl cysteine, citric acid, isocitric acid, ascorbic acid, isoascorbic acid, tartaric acid, malic acid, gluconolactone and other antioxidants may be added to the anthralin formulation to prevent oxidation. The total concentration of the antioxidant(s) may range from about 0.01% to about 5% by weight, with preferred range of about 0.1% to about 2% by weight.

To prepare a typical wax formulation, the wax(es) is first heated until it has completely melted, then mixed with a vehicle selected from isododecane, ethanol, triethyl citrate and other organic solvents, including those previously described for use as a solvent in the anthralin formulation of the present invention. Additional components such as cholesterol, mineral oil, lemon oil, vanillin, coconut oil, and/or emulsifiers, such as polysorbate 80 and sorbitan sesquioleate, may also be added to the wax formulation. The preferred waxes are beeswax, ceresin and paraffin. The total concentration of the wax(es) may range from about 0.01% to about 99.9% by weight, with preferred range of about 1% to about 80% by weight, with more preferred range of about 5% to about 60% by weight and with most preferred range of about 10% to about 40% by weight. The volume concentration of ethanol may range from about 1% to about 60% by weight, with preferred range of about 10% to about 50% by weight, with more preferred range of about 10% to about 40% by weight.

Fine powder, such as talc and starch, may be packaged in a powder can with a dispenser cap. The preferred powders are talc, starch powder, cellulose powder, oatmeal powder, and more preferred ones are fine powders of talc and starch.

To formulate a synergistic or amplified composition, a topical agent(s) may be directly incorporated into a composition containing anthralin. For example, a typical synergistic or amplified composition comprising anthralin and a topical agent was formulated as follows: anthralin 0.25 gram was dissolved in ethanol 22 ml, triethyl citrate 15 ml, butylene glycol 15 ml, isododecane 30 ml, sorbitan sesquioleate 13 ml, oxalic acid 0.5 gram, mandelic acid 0.5 gram, retinyl acetate 1 gram and N-acetyl-L-proline 3 grams. Hydrocortisone 17-valerate 0.2 gram was then added to the formulation as a topical agent. The synergistic composition for treating dermatological disorders such as psoriasis and eczema thus formulated contained 0.25% anthralin, 0.2% corticosteroid, 1% retinoid, and 0.5% alpha hydroxyacid. Alternatively, the topical agent(s) may be applied to skin lesions separately, but substantially contemporaneously, to the anthralin formulation.

In accordance with the present invention, the anthralin formulation is first topically applied to the involved skin area, or skin lesions, such as psoriatic plaques or eczema, of a patient in need of such treatment. The particular concentration of anthralin present in the anthralin formulation will vary depending on the patient, and is generally selected by the treating physician or practitioner using criteria well known in the art, such as severity of disorder experienced by the patient, any known tendency towards anthralin irritation, and the like. When topically treating with anthralin, it is common practice to begin treatment at a low concentration, such as 0.1% or 0.2% by weight anthralin, to avoid unnecessary irritation, and if necessary, gradually increase the concentration of anthralin, depending on the patient's condition and tolerance for the anthralin.

The anthralin formulation may be applied by any means which provides a relatively uniform layer of anthralin formulation on the involved area. Suitable means of application include spraying, roll-on, and application using a brush, saturated cotton gauze, pad, sponge-tipped applicator, and the like.

As the anthralin formulation penetrates into the lesions or evaporates, any unabsorbed anthralin formulation on the lesion surface can be wiped off with a tissue, paper towel, cloth or the like. Thereafter, a wax formulation is applied to the lesion to cover the anthralin formulation-treated area. The wax formulation may be applied using any application method that allows for applying a relatively uniform layer of the wax formulation. Such application methods include, but are not limited to, spraying, roll-on, and application by brush, cotton gauze, pad, sponge-tipped applicator, and the like. As the vehicle(s) of the wax formulation evaporate, a thin film of wax will be formed to cover the lesion surface of the involved area. There are two advantages to the presence of the wax film: (a) the thin wax film will act as an occlusive backing to drive the penetration of anthralin deeper into the lesions; and (b) the wax film will prevent any trace amounts of anthralin from contacting clothing or other objects.

Finally, a powder, such as talc, may then be optionally applied over the wax film in order to eliminate any remaining anthralin thereby further ensuring that staining of clothing or other objects is avoided. Use of a powder in the method of the present invention also serves to increase the patient's comfort, as it acts as a barrier between the patient's garments and the potentially tacky wax film on the skin. The powder may be applied by dusting using a puff or pad, sprinkling, spreading and the like.

In a typical case, the method of the present invention using an anthralin formulation comprising from about 0.1% to about 0.2% by weight anthralin was topically applied by the patient to chronic psoriatic plaques once or twice daily without skin irritation and staining to the skin and clothing. After a few weeks of topical application, psoriatic lesions usually improved substantially; the skin became near normal in appearance after two months of treatment. Without further treatment, the skin stayed clinically free of psoriasis a longer time than skin treated with topical corticosteroids.

The invention will now be illustrated by the following specific, non-limiting examples.

EXAMPLE 1

A.) A typical liquid anthralin formulation was formulated as follows. Anthralin powder 0.25 gram was dissolved in a solvent prepared by mixing ethanol 25 ml, triethyl citrate 15 ml, butylene glycol 15 ml, isododecane 30 ml, sorbitan sesquioleate 15 ml, oxalic acid 0.5 gram. The light yellowish liquid thus formulated contained 0.25% by weight anthralin.

B.) Alternatively, a 0.5% by weight liquid anthralin formulation was formulated by dissolving 0.5 gram anthralin powder in a solvent prepared by mixing ethanol 30 ml, diethyl tartrate 22 ml, triethyl citrate 22 ml, propylene glycol 25 ml, oxalic acid 0.5 gram, N-acetylcysteine 0.5 gram.

EXAMPLE 2

A.) A typical wax formulation was formulated as follows. Beeswax 30 grams was heated to melting, then mixed with isododecane 50 ml and ethanol 20 ml as a vehicle.

B.) Alternatively, beeswax 12 grams was heated to melting, then mixed with isododecane 44 ml and ethanol 44 ml as a vehicle.

C.) In another formulation, beeswax 12 grams was heated to melting, then mixed with isododecane 52 ml, ethanol 25 ml, triethyl citrate 5 ml, mineral oil 3 ml, cholesterol 3 grams as a vehicle.

EXAMPLE 3

The method was typically carried out as follows. A liquid anthralin formulation as formulated in Example 1(A) was topically applied to skin lesions once to twice daily by the patient using a saturated cotton pad. As the anthralin penetrated into the lesions and the solvents evaporated, a tissue or paper towel was used to wipe off excess materials from the surface of the lesions. The wax formulation as formulated in Example 2(B) was topically applied to the lesions. As the vehicles of the wax formulation evaporated, talc powder was applied or dusted onto the lesions. The above system or process prevented the staining of the skin and clothing.

EXAMPLE 4

A female subject, age 21, having guttate psoriasis for two months did not respond to three weeks of treatment with triamcinolone acetonide cream. She started topical application twice daily of the 0.25% by weight anthralin formulation by the method as described in Example 3. After three weeks of the treatment, her skin was entirely free of psoriasis and remained so over a nine-month period.

EXAMPLE 5

A female subject, age 69, having generalized plaque psoriasis for several decades, required treatment with intramuscular injections of methotrexate every one to four weeks to maintain approximately 50% improvement of lesions. She started topical administration of anthralin using the method as described in Example 3 by application, once daily, of an anthralin formulation containing 0.2% anthralin by weight. The concentration of anthralin in the anthralin formulation was gradually increased, over a period of one month, to a final concentration of 1% anthralin by weight. After a few weeks of the topical treatment, her psoriatic lesions started to clear completely, and the need for systemic treatment with methotrexate was reduced to an injection every four to six weeks. Such degree of improvement was thus sustained over more than six months.

EXAMPLE 5

A male subject, age 40, having plaque psoriasis for four years, did not improve well with topical treatment of high potency corticosteroids or calcipotriene (Dovonex). He initiated topical administration of anthralin using the method of the present invention as described in Example 3 by application, once daily, of an anthralin formulation containing 0.2% by weight anthralin. The concentration of anthralin in the anthralin formulation was gradually increased, over a period of one month, to a final concentration of 1% anthralin by weight. The male subject's lesions began to clear within three months of the initial application. His state of approximately 90% improvement of the psoriasis was maintained over a period of one year.

EXAMPLE 7

A female subject, age 40, having generalized small plaque psoriasis for seventeen years did not respond to topical potent corticosteroids and calcipotriene (Dovonex). She started topical administration of anthralin using the method as described in Example 3 by application, once daily, of an anthralin formulation containing 0.3% anthralin by weight. The concentration of anthralin in the anthralin formulation was gradually increased, over a period of one month, to a final concentration of 0.6% anthralin by weight. After four months of the treatment, her skin was approximately 90% free of psoriasis. This was the most beneficial response to psoriasis treatments she had experienced in seventeen years.

EXAMPLE 8

A female subject, age 35, had small plaque psoriasis covering approximately 50% of her body surface for twenty years duration. She started topical application once daily of 3% anthralin formulation, using the method as described in Example 3. After four months of the topical treatment, her psoriatic lesions improved approximately 75%. At the end of five months of topical treatment, the improvement of her skin was the best ever in her memory.

EXAMPLE 9

A male subject, age 77, with chronic plaque psoriasis of elbows, knees and buttocks did not respond to topical corticosteroids. He initiated topical application twice daily of the 0.4% anthralin formulation, using the method as described in Example 3. After three months of the topical treatment, the psoriatic lesions resolved completely and his skin was free of psoriasis.

EXAMPLE 10

Typically, the method was carried out as follows. The patient first applied an anthralin formulation containing 0.25% anthralin to the affected areas of skin using a small, sponge-tipped applicator. He followed with an application of the wax formulation of Example 2(B), applying the wax formulation using a roll-on applicator. He then sprinkled the affected area with fine talc. The patient carried out the above method twice a day for four (4) weeks and experienced no staining of his clothes. After four (4) weeks of treatment, the patient's skin was free of the dermatological disorder.

It will be appreciated by those skilled in the art that changes could be made to the embodiments described above without departing from the broad inventive concept thereof. It is understood, therefore, that this invention is not limited to the particular embodiments disclosed, but is intended to cover modifications within the spirit and scope of the present invention as defined by the appended claims.

We claim:

1. A method of treating dermatological disorders in a human comprising:
   (a) topically applying an anthralin formulation containing a therapeutically effective amount of anthralin to an involved area of the skin of the human, and
   (b) thereafter, topically applying a wax formulation to the involved area, wherein the wax formulation comprises a wax.

2. The method of claim 1 further comprising the step of topically applying a powder to the involved area.

3. The method of claim 2 wherein the powder is selected from the group consisting of talc, starch powder, cellulose powder, oatmeal powder and mixtures thereof.

4. The method of claim 1 wherein the wax formulation further comprises a vehicle.

5. The method of claim 4 wherein the wax is present in the wax formulation at a concentration of about 1% to about 80% by weight.

6. The method of claim 4 wherein the wax is present in the wax formulation at a concentration of about 5% to about 60% by weight.

7. The method of claim 4 wherein the wax is present in the wax formulation at a concentration of about 10% to about 40% by weight.

8. The method of claim 4 where the wax is selected from the group consisting of beeswax, ceresin, paraffin and mixtures thereof.

9. The method of claim 1 wherein anthralin is present in the anthralin formulation at a concentration of about 0.05% to about 10% by weight.

10. The method of claim 1 wherein anthralin is present in the anthralin formulation at a concentration of about 0.1% to about 5% by weight.

11. The method of claim 1 wherein the anthralin is present in the anthralin formulation at a concentration of about 0.1% to about 1% by weight.

12. The method of claim 1 wherein the topical application of the anthralin formulation is in the form selected from the group consisting of a liquid, a lotion, a gel and a cream.

13. The method of claim 12 wherein the topical application is in the form of a liquid comprising anthralin dissolved in a solvent.

14. The method of claim 13 wherein the solvent is selected from the group consisting of ethanol, propylene glycol, butylene glycol, diisopropyl adipate, diethyl tartrate, triethyl citrate, isopropyl myristate, isopropyl palmitate, ethoxy diglycol, isododecane, isohexadecane, and isoeicosane.

15. The method of claim 1 wherein the anthralin formulation further comprises at least one antioxidant.

16. The method of claim 15 wherein the at least one antioxidant is present at a concentration of about 0.1% to 5% by weight.

17. The method of claim 1 wherein the anthralin formulation further comprises at least one topical agent selected from the group consisting of hydrocortisone, hydrocortisone 21-acetate, hydrocortisone 17-valerate, hydrocortisone 17-butyrate, triamcinolone acetonide, betamethasone dipropionate, clobetasol propionate, salicylic acid, retinoic acid, retinyl acetate, alpha hydroxyacids, O-acetyl alpha hydroxyacids, N-acetyl amino acids and vitamin E acetate.

18. The method of claim 1 wherein the anthralin formulation further comprises at least one topical agent selected from the group consisting of antipsoriatic agents, antieczema agents, antidermatitis agents, antiwart agents, antihyperkeratotic agents, antikeratoses agents, antidandruff agents, antiseborrheic agents, antihistamines, antipruritic agents, antiinflammatory agents, antimicrobial agents, corticosteroids, retinoids, coal tar and vitamins.

19. The method of claim 1 wherein the anthralin formulation further comprises at least one topical agent selected from the group consisting of mandelic acid, citric acid, gluconolactone O-acetyl-mandelic acid, tartaric acid, malic acid, urea, selenium sulfide and zinc pyrithione.

* * * * *